United States Patent [19]

Wachi et al.

[11] Patent Number: 5,334,760

[45] Date of Patent: Aug. 2, 1994

[54] METHOD OF PRODUCING A PHOSPHINYL-CARBOXYLIC ACID DERIVATIVE

[75] Inventors: Toshio Wachi, Nara; Yutaka Sakaguchi, Kitakatsuragi; Kotaro Fujita, Sakai, all of Japan

[73] Assignee: Sakai Chemical Industry Co., Ltd., Osaka, Japan

[21] Appl. No.: 925,830

[22] Filed: Aug. 7, 1992

[30] Foreign Application Priority Data

Aug. 9, 1991 [JP] Japan .................. 3-287421
Jun. 19, 1992 [JP] Japan .................. 4-161450

[51] Int. Cl.$^5$ .................. C07F 9/52; C07F 9/50; C07F 9/535
[52] U.S. Cl. .................. 562/817; 562/24; 562/819; 562/842
[58] Field of Search .................. 562/819, 24, 817, 842

[56] References Cited

U.S. PATENT DOCUMENTS

| | | | |
|---|---|---|---|
| 3,259,671 | 7/1966 | Jungermann et al. | 562/819 |
| 4,022,826 | 5/1977 | Lohmar et al. | 260/543 P |
| 4,081,463 | 3/1978 | Birum et al. | 562/24 |
| 4,096,182 | 6/1978 | Rupp et al. | 260/544 Y |
| 4,318,865 | 3/1982 | Ohorodnik et al. | 260/543 F |
| 4,503,178 | 3/1985 | Green | 568/12 |
| 4,613,699 | 9/1986 | Green | 568/15 |
| 4,623,687 | 11/1986 | Green | 568/12 |
| 4,769,182 | 9/1988 | Hazen | 562/24 |
| 5,153,345 | 10/1992 | Knorr et al. | 558/179 |

OTHER PUBLICATIONS

CA67:32744v (1967).

Primary Examiner—José G. Dees
Assistant Examiner—B. Frazier
Attorney, Agent, or Firm—Nikaido Marmelstein Murray & Oram

[57] ABSTRACT

A phosphine derivative of the following general formula (I):

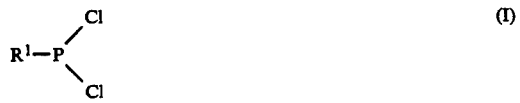

(wherein $R^1$ is an alkyl group having 1 to 18 carbon atoms or an aryl group having 6 to 18 carbon atoms, and the aryl group may have an alkyl group having 1 to 18 carbon atoms or an alkenyl group having 2 to 18 carbon atoms) is reacted with acrylic acid or methacrylic acid in the presence of a catalyst selected from the group consisting of an organic peroxide and an azo-compound, and the resulting reaction product is hydrolyzed with water, thereby to obtain a phosphinyl-carboxylic acid derivative of the following general formula (III):

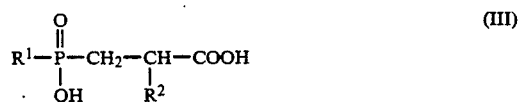

(wherein $R^1$ is as defined above, and $R^2$ is a hydrogen atom or a methyl group). Based on the reaction above-mentioned, ester of free acid and a cyclic acid anhydride can also be obtained. Accordingly, the target compound can be obtained at a relatively low reaction temperature in a short period of time with high yield. The reaction proceeds substantially quantitatively, thus enhancing the productivity and facilitating the purification.

4 Claims, No Drawings

METHOD OF PRODUCING A PHOSPHINYL-CARBOXYLIC ACID DERIVATIVE

BACKGROUND OF THE INVENTION

The present invention relates to a new method of producing a phosphinyl-carboxylic acid derivative (or phosphinic acid derivative) which can be used as a flame-retardant for polyester or a bi-functional reactive flame-retardant, or an intermediate thereof.

Conventionally, a phosphinyl-carboxylic acid derivative has been produced by the following reaction set forth in Zhural Obsh. khim. 37, 455–460, 1967 (C.A. 67, 32744 v).

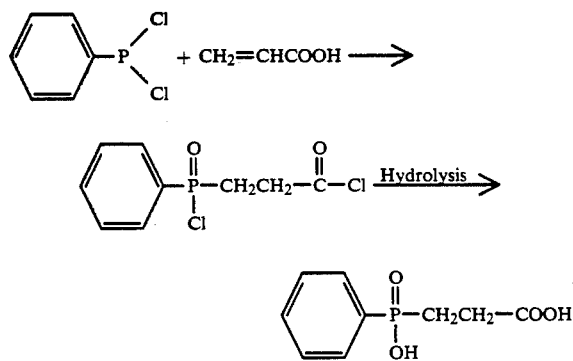

In this method using no catalyst, however, the reaction takes a long period of time (about 15 days at room temperature) and the yield is as low as about 71%. Thus, this method is not suitable for industrial application.

To overcome such defects, U.S. Pat. No. 4,081,463 has proposed the use of an excessive amount of acrylic acid to improve the yield. However, such a method is disadvantageous in view of effluent disposal due to excessive use of acrylic acid.

SUMMARY OF THE INVENTION

It is a main object of the present invention to provide an industrially applicable method of producing a phosphinyl-carboxylic acid derivative, by which the reaction proceeds substantially quantitatively and by which an object product with high purity can be obtained with high yield.

A first producing method in accordance with the present invention comprises the steps of:

reacting a phosphine derivative of the following general formula (I):

$$R^1-P\begin{matrix}\diagup Cl\\ \diagdown Cl\end{matrix} \quad (I)$$

(wherein $R^1$ is an alkyl group having 1 to 18 carbon atoms or an aryl group having 6 to 18 carbon atoms, and the aryl group may have an alkyl group having 1 to carbon atoms or an alkenyl group having 2 to 18 carbon atoms)

with acrylic acid or methacrylic acid of the following general formula (II):

$$CH_2=C-COOH \atop | \atop R^2 \quad (II)$$

(wherein $R^2$ is a hydrogen atom or a methyl group)

in the presence of a catalyst selected from the group consisting of an organic peroxide and an azo-compound; and hydrolyzing the resulting reaction product with water to obtain a phosphinyl-carboxylic acid derivative of the following general formula (III):

$$R^1-\underset{OH}{\underset{|}{P}}-CH_2-\underset{R^2}{\underset{|}{CH}}-COOH \atop \overset{O}{\overset{\|}{}} \quad (III)$$

(wherein $R^1$ and $R^2$ are as defined above).

More specifically, the present invention uses a specific catalyst serving as a free-radical generating source, thus giving, with high yield, a phosphinyl-carboxylic acid derivative of the general formula (III). According to the present invention, the reaction can be carried out at a relatively low temperature in a short period of time, and the resulting product (III) is of high purity. Further, according to the present invention, it is not required to use an excessive amount of either one of the starting materials and the reaction can proceed without a solvent. This improves the reactor efficiency or productivity, and facilitates effluent disposal. Further, since the reaction proceeds substantially quantitatively, the product can be readily purified.

Examples of the aryl group include phenyl, naphthyl, anthryl and phenanthryl groups.

A second producing method in accordance with the present invention comprises the steps of:

reacting a phosphine derivative of the general formula (I) above-mentioned with acrylic acid or methacrylic acid of the general formula (II) above-mentioned in the presence of a catalyst selected from the group consisting of an organic peroxide and an azo-compound; and reacting the resulting reaction product with a hydroxyl group-containing compound of the following general formula (IV):

$$R^3-OH \quad (IV)$$

(wherein $R^3$ is an alkyl group having 1 to 10 carbon atoms or an aryl group having 6 to 18 carbon atoms and the aryl group may contain an alkyl group having 1 to 18 carbon atoms or an alkenyl group having 2 to 18 carbon atoms), thereby to obtain a phosphinyl-carboxylic acid derivative in the form of ester represented by the following general formula (V):

$$R^1-\underset{OR^4}{\underset{|}{P}}-CH_2-\underset{R^2}{\underset{|}{CH}}-COOR^3 \atop \overset{O}{\overset{\|}{}} \quad (V)$$

(wherein $R^1$, $R^2$ and $R^3$ are as defined above $R^4$ is a hydrogen atom, an alkyl group having 1 to 10 carbon atoms or an aryl group having 6 to 18 carbon atoms, and the aryl group may contain an alkyl group having 1 to 18 carbon atoms or an alkenyl group having 2 to 18 carbon atoms).

Likewise the phosphinyl-carboxylic acid derivative of the general formula (III), the phosphinyl-carboxylic acid derivative in the form of ester of the general formula (V) can be reacted with high yield in a short period of time at a low temperature. The phosphinyl-carboxylic acid derivative (V) in the form of ester, can be used as a flame-retardant for polyester or a bi-functional reactive flame-retardant, or an intermediate thereof. Further by hydrolyzing this derivative, there can be readily obtained, as its free acid, the phosphinyl-carboxylic acid derivative of the general formula (III). Since the ester (V) is generally in the form of a liquid, the reaction can proceed while the gas of hydrogen chloride generated at esterification is distilled away under reduced pressure. This advantageously shortens or eliminates the subsequent water washing step and produces a product of high purity.

A third producing method in accordance with the present invention comprises the steps of:

reacting the phosphine derivative of the general formula (I) above-mentioned with acrylic acid or methacrylic acid of the general formula (II) above-mentioned in the presence of a catalyst selected from the group consisting of an organic peroxide and an azo-compound; and reacting the resulting reaction product with an acetic anhydride to obtain a phosphinyl-carboxylic acid derivative in the form of a cyclic acid anhydride represented by the following general formula (VI):

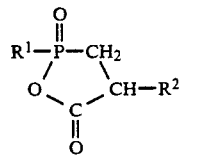
(VI)

(wherein $R^1$ and $R^2$ are as defined above).

The cyclic acid anhydride of the general formula (VI) has the same effect as that produced by the ester above-mentioned. This anhydride itself can be used as a flame-retardant for polyester or a bi-functional reactive flame-retardant, or an intermediate thereof. Further, by hydrolyzing this anhydride, there can be readily obtained, as its free acid, the phosphinyl-carboxylic acid derivative of the general formula (III). Likewise the ester (V), this cyclic acid anhydride (VI) is generally in the form of a liquid and therefore advantageous in view of efficient productivity and high purity.

Other and further objects, features and advantages of the invention will appear more fully from the following description.

DETAILED DESCRIPTION OF THE INVENTION

The following description will discuss in more detail the method of producing each of the phosphinyl-carboxylic acid derivatives (III), (V) and (VI).

[A] Method of producing the phosphinyl-carboxylic acid derivative of the general formula (III)

Examples of the organic peroxide used as the catalyst include t-butyl peroxybenzoate, t-butyl peroxyacetate, t-butyl peroxylaurate, di-t-butyl peroxyisophthalate, t-butyl peroxypivalate, t-butyl peroxyisobutyrate, t-butyl peroxy(2-ethylhexanoate), cumyl peroxyneodecanoate, t-butyl peroxymaleic acid, t-butyl peroxyisopropyl carbonate, t-butyl peroxyneohexanoate, benzoyl peroxide, acetyl peroxide, octanoyl peroxide, decanoyl peroxide, lauroyl peroxide, succinic acid peroxide, methyl ethyl ketone peroxide, cyclohexanone peroxide, acetylacetone peroxide, 1,1-bis(t-butyl peroxy)cyclohexane, t-butyl hydro-peroxide, di-t-butyl peroxide, dicumyl peroxide, 2,5-dimethyl-2,5-di(t-butyl peroxy)hexane and the like.

According to the present invention, there can be used, as the azo-compound, any of azo-compounds to be used as an initiater in a normal radical polymerization reaction.

Examples of the azo-compound include 2,2'-azobisisobutyronitrile, 2,2'-azobisisopentanitrile, 2,2'-azobisisohexanitrile, 2,2'-azobis-2,4-dimethylvaleronitrile, 4,4'-azobis-4-cyanovaleric acid, 1,1'-azobis-1-cyclohexane carbonitrile, dimethyl-2,2'-azobisisobutyrate, 2,2'-azobis(2-amidinopropane)dihydrochloride and the like.

The catalyst is used in an amount of about 0.1 to 3% by mole, preferably 0.2 to 2% by mole, for 1 mole of the compound of the general formula (I). The molar ratio of the compound of the general formula (I) to the compound of the general formula (II) may be generally equal to 1:1. However, the compound of the general formula (II) may be used more than the compound of the general formula (I) as far as it does not cause trouble as to payability, effluent disposal and the like.

When an organic peroxide is used as the catalyst when reacting the compound of the general formula (I) with the compound of the general formula (II), a mixture of the compound of the general formula (I) and the organic peroxide is previously prepared and heated to 50° to 60° C., and the compound of the general formula (II) is then added dropwise to the mixture. During the dropwise addition, heat is generated. Accordingly, the reaction temperature is maintained, during such addition, at 60° to 90° C., preferably at 60° to 75° C. After the dropwise addition, the reaction is carried out at a temperature of 60° to 90° C., preferably 60° to 75° C., generally for 1 to 3 hours, and comes to an end. On the other hand, when the azo-compound is used as the catalyst, a mixture of the compound of the general formula (I) and the azo-compound is previously prepared and heated to 70° to 80° C., and the compound of the general formula (II) is then added dropwise to the mixture. During the dropwise addition, heat is generated. Accordingly, the reaction temperature is maintained, during such addition, at 80° to 110° C., preferably at 85° to 100° C. After the dropwise addition, the reaction is carried out at a temperature of 80° to 110° C., preferably 85° to 100° C., generally for 2 to 7 hours, and comes to an end.

The reaction proceeds generally without a solvent. As necessary, however, the reaction may be carreid out in a solvent. Examples of a solvent which can be used, include solvents of the hydrocarbon type such as n-hexane, toluene, xylene, chlorobenzene and the like.

Then, the resulting reaction product is hydrolyzed in the following manner. With the reaction product wherein water is added at a molar amount of 5 to 20 times of the reaction product or with the reaction product dropped in water having the same molar amount as the above, a reaction is carried out at a temperature of 0° to 100° C. for 1 to 3 hours. After completion of the reaction, the resulting reaction product is cooled under stirring, so that a crystal is deposited. By a thin-layer chromatography, it is made sure that this crystal contains, besides the main component, a trace amount of impurities (two types) only. At this stage, the crude yield is not less than 95% and the reaction proceeds substantially quantitatively.

By recrystallization or the like, the phosphinyl-carboxylic acid derivative (III) can be collected also from the filtrate after the crystal above-mentioned has been deposited.

For more perfect purification of the phosphinyl-carboxylic acid derivative (III) as the final product, the crystal thereof is washed with water at least one time and then dried to give a phosphinyl-carboxylic acid derivative (III) of higher purity.

Examples of the phosphine derivative of the general formula (I) serving as a starting material include dichloro(phenyl)phosphine, dichloro(o-methylphenyl)phosphine, dichloro(m-methylphenyl)phosphine, dichloro(p-methylphenyl)phosphine, dichloro(p-ethylphenyl)phosphine, dichloro(p-propylphenyl)phosphine, dichloro(p-butylphenyl)phosphine, dichloro(p-octylphenyl)phosphine, dichloro(p-dodecylphenyl)phosphine, dichloro(p-octadecylphenyl)phosphine, dichloro(p-octadecenylphenyl)phosphine, dichloro(methyl)phosphine, dichloro(ethyl)phosphine, dichloro(propyl)phosphine, dichloro(butyl)phosphine, dichloro(decyl)phosphine, dichloro(tetradecyl)phosphine, dichloro(octadecyl)phosphine, dichloro(p-vinylphenyl)phosphine, dichloro(m-vinylphenyl)phosphine, dichloro(o-vinylphenyl)phosphine, dichloro(p-allylphenyl)phosphine, dichloro(o-allylphenyl)phosphine, dichloro[p-(1-butenyl)phenyl]phosphine, dichloro[p-(2-hexenyl)phenyl]phosphine, dichloro[p-(2-nonenyl)phenyl]phosphine, dichloro[p-(2-dodecenyl)phenyl]phosphine and the like.

Examples of the phosphinyl-carboxylic acid derivative of the general formula (III) as the final reaction product include 3-[hydroxy(phenyl)phosphinyl]propionic acid, 3-[hydroxy(p-methylphenyl)phosphinyl]propionic acid, 3-[hydroxy(p-ethylphenyl)phosphinyl]propionic acid, 3-[hydroxy(p-propylphenyl)phosphinyl]propionic acid, 3-[hydroxy(p-butylphenyl)phosphinyl]propionic acid, 3-[hydroxy(p-octylphenyl)phosphinyl]propionic acid, 3-[hydroxy(p-dodecylphenyl)phosphinyl]propionic acid, 3-[hydroxy(p-octadecylphenyl) phosphinyl]propionic acid, 3-[hydroxy(p-octadecenylphenyl)phosphinyl]propionic acid, 3-hydroxy(phenyl)phosphinyl] -2-methylpropionic acid, 3-[hydroxy(p-methylphenyl)phosphinyl]-2-methylpropionic acid, 3-[hydroxy(p-ethylphenyl)phosphinyl]-2-methylpropionic acid, 3-[hydroxy(p-propylphenyl)phosphinyl]-2-methylpropionic acid, 3-[hydroxy(p-butylphenyl)phosphinyl]-2-methylpropionic acid, 3-[hydroxy(p-octylphenyl)phosphinyl]-2-methylpropionic acid, 3-[hydroxy(p-dodecylphenyl)phosphinyl]-2-methylpropionic acid, 3-[hydroxy(p-octadecylphenyl)phosphinyl]-2-methylpropionic acid, 3-[hydroxy (p-octadecenylphenyl)phosphinyl]-2-methylpropionic acid, 3-[hydroxy(m-methylphenyl)phosphinyl]-2-methyl propionic acid, 3-[hydroxy(o-methylphenyl)phosphinyl]-2-methyl propionic acid, 3-[hydroxy(methyl)phosphinyl]propionic acid, 3-[hydroxy(ethyl)phosphinyl]propionic acid, 3-[hydroxy(butyl)phosphinyl]propionic acid, 3-[hydroxy(dodecyl)phosphinyl]propionic acid, 3-[hydroxy(tetradecyl)phosphinyl]propionic acid, 3-[hydroxy(octadecyl)phosphinyl]propionic acid, 3-[hydroxy(p-vinylphenyl)phosphinyl]propionic acid, 3-[hydroxy(m-vinylphenyl)phosphinyl]propionic acid, 3-[hydroxy(o-vinylphenyl)phosphinyl]propionic acid, 3-[hydroxy(p-allylphenyl)phosphinyl]propionic acid, 3-[hydroxy[p-(2-butenyl) phenyl) phosphinyl]propionic acid, 3-[hydroxy[p-(2-hexenyl)phenyl]phosphinyl]propionic acid, 3-[hydroxy[p-(3-dodecenyl)phenyl)phosphinyl] propionic acid and the like.

As other method, the phosphinyl-carboxylic acid derivative (III) can also be obtained by hydrolyzing its ester (V) or the cyclic acid anhydride (VI) as mentioned earlier. The conditions for hydrolysis will be discussed later.

[B] Method of producing the phosphinyl-carboxylic acid derivative of the general formula (V) in the form of ester The compound of the general formula (I) above-mentioned is reacted with the compound of the general formula (II) in the same manner as above-mentioned, and the resulting reaction product is reacted with the hydroxyl group-containing compound of the general formula (IV), thereby to obtain the ester of the general formula (V). The hydroxyl group-containing compound (IV) is used in an amount at molar ratio of at least 2 times, preferably 2 to 4 times, to the amount of the dichloro phosphine derivative which is the starting material. Since heat is generated, the hydroxyl group-containing compound (IV) is added dropwise while cooling the reaction liquid to maintain the liquid temperature at 0° to 30° C. After the dropwise addition, the reaction product is heated and refluxed at a temperature of 50° to 130° C. for 1 to 5 hours. Then, the pressure is gently reduced at the same temperature and finally reduced to 30 mmHg for 1 hour to distil the distillate and gas of hydrogen chloride away. Since the resulting ester is generally in the form of a liquid, the produced gas of hydrogen chloride can be distilled away in the same tank under reduced pressure.

When $R^3$ in the hydroxyl group-containing compound of the general formula (IV) is an alkyl group, the hydroxyl group-containing compound is alcohol having 1 to 10, preferably 1 to 4, carbon atoms, examples of which include methanol, ethanol, isopropanol, n-propanol, n-butanol, t-butanol and the like. When $R^3$ is an aryl group, examples of the aryl group include phenyl, naphtyl, anthryl and phenanthryl groups. Examples of the hydroxyl group-containing compound in which $R^3$ is an aryl group, include phenol, cresol, ethylphenol, propylphenol, vinylphenol, allylphenol, 1-butenylphenol, $\alpha$-naphthol, $\beta$-naphthol, 1-anthrol, 2-phenanthrol and the like.

The reaction is conducted without a solvent, but a solvent may be used as necessary. Generally, the yield is 95% or more and substantially quantitative.

There are mixingly produced (i) ester containing a hydrogen atom as $R^4$ in its general formula (V) and (ii) ester containing other group than the hydrogen atom (for example, an alkyl group) as $R^4$ in its general formula (V). The product esters may be subjected, as mingled in this manner, to the subsequent steps including hydrolysis and the like, or the respective compounds may be separated by predetermined separating means. Alternatively, the reaction conditions may be so arranged as not to produce a mixture of both-type esters, but as to produce either ester only with higher yield.

Examples of the phosphinyl-carboxylic acid derivative of the general formula (V) in the form of ester, include methyl 3-[hydroxy(phenyl)phosphinyl]propionate, methyl 3-[methoxy(phenyl)phosphinyl]propionate, butyl 3-[hydroxy(phenyl)phosphinyl]propionate, butyl 3-[butoxy(phenyl)phosphinyl]propionate, decyl 3-[hydroxy(phenyl)phosphinyl]propionate, decyl 3-[decyloxy(phenyl)phosphinyl]propionate, t-butylphenyl 3-[hydroxy(phenyl)phosphinyl]propionate, t-butylphenyl 3-[t-butoxy(phenyl)phosphinyl]propionate, methyl 3-[hydroxy(p-methylphenyl)phosphinyl]propionate, methyl 3-[methoxy(p-methylphenyl)phosphinyl]propionate, methyl 3-[hydroxy(o-vinylphenyl)phosphinyl]propionate, methyl 3-[methoxy(o-vinylphenyl)phosphinyl]propionate, methyl 3-[hydroxy(ethyl)phosphinyl]propionate, methyl 3-[methoxy(ethyl)phosphinyl]propionate, butyl 3-[hydroxy(butyl)phosphinyl]propionate, butyl 3-[butoxy(butyl)phosphinyl]propionate, propyl 3-[hydroxy(octyl)phosphinyl]propionate, propyl 3-[propoxy(octyl)phosphinyl]propionate, phenyl 3-[hydroxy(dodecyl)phosphinyl]propionate, phenyl 3-[phenoxy(dodecyl)phosphinyl]propionate, p-vinylphenyl 3-[hydroxy(dodecyl)phosphinyl]propionate, p-vinylphenyl 3-[p-vinylphenoxy(dodecyl)phosphinyl]propionate, p-hexenylphenyl 3-[hydroxy(dodecyl)phosphinyl]propionate, m-hexenylphenyl 3-[m-hexenylphenoxy(dodecyl)phosphinyl]propionate.

The hydrolysis of the ester of the general formula (V) is carried out in the manner that the ester (V) is added to water which is in a molar ratio of 5 to 20 times of the amount of the ester (V), or that the ester (V) is dropped in water at the same molar ratio as the above. The reaction is carried out at a temperature of 0° to 100° C. for about 1 to about 3 hours. After the reaction is completed, the resulting reaction product is cooled under stirring, so that a crystal is deposited. The reaction product may be purified in any of the following manners. When alcohol having 1 to 3 carbon atoms has been used at the time of esterification, the alcohol is first distilled away and the crystal is then filtered off and dried. When other hydroxyl group-containing compound than the alcohol having 1 to 3 carbon atoms has been used at the time of esterication, the reaction product is first washed with a solvent of the hydrocarbon type such as n-hexene, toluene, xylene or the like, and then dried. Generally, the yield is 93% or more.

As the catalyst for hydrolysis of ester, mineral acid such as sulfuric acid, hydrochloric acid or the like may be used. The mineral acid is used in an amount of 0.1 to 10.0% by weight, preferably from 0.5 to 1.0% by weight, of the ester.

[C] Method of producing the phosphinyl-carboxylic acid derivative in the form of a cyclic acid anhydride of the general formula (VI)

The compound of the general formula (I) above-mentioned is reacted with the compound of the general formula (II) in the same manner as above-mentioned, and the resulting reaction product is reacted with acetic anhydride to obtain the cyclic acid anhydride of the general formula (VI). The acetic anhydride is used in an amount at molar ratio of 1 to 3 times, preferably 1 to 2 times, that the amount of the reaction product. The reaction is conducted at a temperature of 50° to 100° C. for 1 to 10 hours, preferably at a temperature of 50° to 80° C. for 1 to 5 hours. The by-product or acetyl chloride and the residual acetic anhydride are distilled away under reduced pressure.

Examples of the cyclic acid anhydride of the general formula (VI) include the compounds shown in Table 1.

TABLE 1

$$R^1-\underset{\underset{O}{|}}{\overset{\overset{O}{\|}}{P}}-CH_2$$
$$\quad\quad O\diagdown\underset{\|}{C}\diagup CH-R^2$$
$$\quad\quad\quad\quad\, O$$

| $R^1$ | $R^2$ |
|---|---|
| $CH_3-$ | H |
| $CH_3(CH_2)_2CH_2-$ | H |
| $CH_3(CH_2)_{10}CH_2-$ | H |
| phenyl- | H |
| $(CH_3)_3C-$ | H |
| $CH_3-$ | $CH_3-$ |
| $CH_3(CH_2)_2CH_2-$ | $CH_3-$ |
| $CH_3(CH_2)_{10}CH_2-$ | $CH_3-$ |
| phenyl- | $CH_3-$ |
| $(CH_3)_3C-$ | $CH_3-$ |
| $CH_3-$C$_6$H$_4-$ | H |
| $C_2H_5-$C$_6$H$_4-$ | $CH_3-$ |
| $CH_2=CH-$C$_6$H$_4-$ | H |
| $C_2H_5-CH=CH-$C$_6$H$_4-$ | $CH_3-$ |

The reaction in which the cyclic acid anhydride of the general formula (VI) is hydrolyzed to obtain the phosphinyl-carboxylic acid derivative of the general formula (III), can be carried out in the same manner as in the hydrolysis of the ester derivative of the general formula (V). Generally, the yield is 93% or more.

As thus discussed, the method of producing a phosphinyl-carboxylic acid derivative of the present invention comprises the steps of reacting a specific phosphine derivative with acrylic acid or methacrylic acid in the presence of a catalyst selected from the group consisting of an organic peroxide and an azo-compound, and hydrolyzing the resulting reaction product, so that a highly pure phosphinyl-carboxylic acid derivative (III) is produced at a relatively low reaction temperature in a short period of time with high yield. According to the present invention, it is not necessary to use an excessive amount of either one of the starting raw materials, thus eliminating troubles as to effluent disposal and the like.

The reaction can be carried out without a solvent, thus improving the reactor efficiency or productivity. Further, since the reaction proceeds substantially quantitatively, the product can be readily purified. Accordingly, the phosphinyl-carboxylic acid derivative of the general formula (III) produced by the method of the present invention can be suitably used as a flame-retardant or its intermediate.

Any of the methods of producing the phosphinyl-carboxylic acid derivative of the general formula (V) in the form of ester, and the phosphinyl-carboxylic acid derivative of the general formula (VI) in the form of a cyclic acid anhydride, has the advantages of the method of producing the phosphinyl-carboxylic acid derivative of the general formula (III) in the form of free acid. Since the reaction product (V) is generally in the form of a liquid, the esterification can proceed in the same tank while the gas of hydrogen chloride is distilled away under reduced pressure. This advantageously shortens or eliminates the subsequent water washing step and therefore readily produces a product of high purity.

EXAMPLES

The following description will discuss the method of producing a Phosphinyl-carboxylic acid derivative of the present invention with reference to examples thereof. However, the present invention should not be limited to these examples only.

EXAMPLE 1

A 3-l four neck flask having a Dimroth condenser and a thermometer was charged with 1252.9 g (7.0 moles) of dichloro(phenyl)phosphine and 8.0 g (0.041 mole) of t-butyl peroxybenzoate, and heated under stirring to raise the liquid temperature to 55° C. Then, 504.4 g (7.0 moles) of acrylic acid was added dropwise to the mixture in one hour. To prevent heat from being generated during the dropwise addition, the reaction product was cooled with water to maintain the liquid temperature at 65° to 70° C. After the dropwise addition, the reaction was further continued at the same temperature for 2 hours.

After completion of the reaction, 2.3 l of water was gradually added to the reaction product with the liquid temperature maintained at 50° C. To prevent heat from being generated during this addition, the reaction product was cooled with ice water to maintain the liquid temperature at 60° to 70° C. After the addition, the reaction product was continuously stirred at the same temperature for one hour. After the liquid temperature was cooled to 10° C., the reaction product was filtered off and the resulting crystal was washed with water and then dried by a vacuum oven (60° C.) to obtain 1412.2 g of 3-[hydroxy(phenyl)phosphinyl]propionic acid in the form of a white crystal (yield: 94.2%).

Analytical Values

Melting Point 155° to 157° C. P (%) 14.3 (Calculated value 14.5). Acid value (KOHmg/g) 523.8 (Calculated value 524.3). IR 3044 cm$^{-1}$ (—COOH), 1730 cm$^{-1}$ (C=O) , 1600 (—C$_6$H$_5$). NMR (1H–60 MHz) δ: 0.6–2.7 (m, 4H—CH$_2$CH$_2$—), 7.4–8.1(m, 5H, —CH$_6$H$_5$).

EXAMPLE 2

The reaction was carried out in the same manner as in Example 1 except for the use of 1351.0 g (7.0 moles) of dichloro (p-methylphenyl) phosphine instead of 1252.9 g (7.0 moles) of dichloro(phenyl)phosphine, thereby to obtain 1500.2 g of 3-[hydroxy(p-methylphenyl)phosphinyl]propionic acid in the form of a white crystal (yield: 94.0% ).

Analytical Values

P (%) 13.4 (Calculated value 13.6). Acid value (KOHmg/g) 491.6 (Calculated value 491.7).

EXAMPLE 3

The reaction was carried out in the same manner as in Example 1 except for the use of 602.6 g (7.0 moles) of methacrylic acid instead of 514.7 g (7.0 moles) of acrylic acid, thereby to obtain 1490.2 g of 3-[hydroxy(phenyl)phosphinyl]-2-methylpropioic acid in the form of a white crystal (yield: 93.3%).

Analytical Values

P (%) 13.5 (Calculated value 13.6). Acid value (KOHmg/g) 486.3 (Calculated value 491.7).

EXAMPLE 4

A 3-l four neck flask having a Dimroth condenser and a thermometer was charged with 1252.9 g (7.0 moles) of dichloro(phenyl)phosphine and 8.3 g (0.0506 mole) of azobisisobutyronitrile, and heated under stirring to raise the liquid temperature to 75° C. Then, 514.7 g (7.0 moles) of acrylic acid was added dropwise to the mixture in one hour. During such dropwise addition, heat was gradually generated, but the liquid temperature was maintained at 85° to 90° C. After the dropwise addition, the reaction was further continued at 90° C. for 6 hours.

After completion of the reaction, 2.3 lof water was gradually added to the reaction product with the liquid temperature maintained at 50° C. To prevent heat from being generated during this addition, the reaction product was cooled with ice water to maintain the liquid temperature at 60° to 70° C. After the addition, the reaction product was continuously stirred at the same temperature for one hour. After the liquid temperature was cooled to 10° C., the reaction product was filtered off and the resulting crystal was washed with water and then dried by a vacuum oven (60° C.), thereby to obtain 1403.2 g of 3-[hydroxy(phenyl)phosphinyl]propionic acid in the form of a white crystal (yield: 93.6%).

Analytical Values

P (%) 14.2 (Calculated value 14.5). Acid value (KOHmg/g) 523.7 (Calculated value 524.3).

COMPARATIVE EXAMPLE

A four neck flask was charged with 17.9 g (0.1 mole) of dichloro(phenyl)phosphine, of which temperature was then raised to 55° C. Then, 7.2 g (0.1 mole) of acrylic acid was added dropwise into the flask. The resulting mixture was reacted at 120° C. for 7 hours.

After completion of the reaction, 40 ml of water was gradually added to the reaction product. To prevent heat from being generated during this addition, the reaction product was cooled with ice water to maintain the liquid temperature at 50° to 60° C. After the dropwise addition, the reaction product was continuously stirred at the same temperature for one hour. After the liquid temperature was cooled to 10° C., the reaction product was filtered off and the resulting crystal was washed with water. The crystal was further washed with toluene to remove phenylphosphinic acid which was considered to be by-produced. The crystal was then dried to obtain 15.0 g of 3-[hydroxy-(phenyl)phosphinyl]propionic acid in the form of a crystal (yield: 70.0% ). As a result of analysis of a thin-layer chromatography, the toluene washings contained no 3-[hydroxy(phenyl)phosphinyl]propionic acid.

Analytical Values

Melting Point 150° to 153° C. P (%) 14.0 (Calculated value 14.5). Acid value (KOHmg/g) 510.8 (Calculated value 524.3).

EXAMPLE 5

A 3-l four neck flask having a Dimroth condenser and a thermometer was charged with 895.0 g (5.0 moles) of dichloro(phenyl)phosphine and 5.8 g (0.030 mole) of t-butyl peroxybenzoate, and heated under stirring to raise the liquid temperature to 55° C. Then, 360.3 g (5.0 moles) of acrylic acid was added dropwise to the mixture in one hour. To prevent heat from being generated during the dropwise addition, the reaction product was cooled with water to maintain the liquid temperature at 65° to 70° C. After the dropwise addition, the reaction was further continued at a temperature of 70° to 75° C. for 2 hours.

After completion of the reaction, the reaction product was cooled with water to lower the liquid temperature to 15° C. Then, 778.3 g (10.5 moles) of n-butanol was added dropwise to the reaction product in 80 minutes. Such dropwise addition was carried out while gradually reducing the pressure in order to remove gas of hydrogen chloride to be generated and while cooling the reaction product in order to lower the liquid temperature to 15° to 20° C. After the drop-wise addition, the reaction was continued at the same temperature for 30 minutes. Then, the liquid temperature was raised and the reaction product was refluxed at 120° C. for 2 hours. At 85° C., an excessive part of n-butanol was distilled away under 3 mmHg, thereby to obtain 1582.9 g of butyl 3-[butoxy(phenyl)phosphinyl]propionate in the form of a colorless transparent liquid (yield: 97.0%).

Analytical Values

P (%) 9.4 (Calculated value 9.5). Refractive index $n_D$=1.4942 (25° C). IR 1740 cm$^{-1}$ (C=O), 1600 cm$^-$(—$C_6H_5$). NMR (1H–60 MHz) δ: 0.9(t, 6H,—$CH_3$), 1.2–1.7(m, 8H, —$CH_2CH_2$—), 1.7–2.9(m, 4H, —$CH_2CH_2$—), 4.0(t, 4H, —$CH_2$—), 7.4–8.1(m, 5H, —$C_6H_5$).

EXAMPLE 6

A 3-l four neck flask having a Liebig condenser and a thermometer was charged with 1142.3 g (3.5 moles) of butyl 3-[butoxy(phenyl)phosphinyl]propionate obtained in Example 5, and under stirring, 530 g of water and a sulfuric-acid aqueous solution containing 5.7 g of sulfuric acid dissolved in 100 g of water were added. The resulting mixture was heated to raise the liquid temperature to 100° C. The reaction was continued for 6 hours while distilling water and butanol away and while replenishing the same amount of distilled water through a dropping funnel.

The reaction product was allowed to stand overnight, and then filtered off. The resulting crystal was washed with water and dried by a vacuum oven (60° C.), thereby to obtain 728.6 g of 3-[hydroxy(phenyl)phosphinyl]propionic acid in the form of a white crystal (yield: 97.2%). The total yield from dichloro(phenyl)phosphine was 94.3%.

Analytical Values

Melting point 155° to 157° C. P (%) 14.2 (Calculated value 14.5). Acid value (KOHmg/g) 523.4 (Calculated value 524.3). IR 3044 cm$^{-1}$ (—COOH), 1730 cm$^{-1}$ (C=O) , 1600 cm$^{-1}$ (—$C_6H_5$). NMR (1H–60 MHz) δ: 1.6–2.7(m, 4H,—$CH_2CH_2$—), 7.4–8.1(m, 5H, —$C_6H_5$).

EXAMPLE 7

The reaction was carried out in the same manner as in Example 5 except for the use of 480 g (15.0 moles) of methanol instead of n-butanol. Then, 873 g of water was added to the resulting reaction product (methyl ester) in its entirety. The liquid temperature was raised to 100° C., and the reaction was continued for 5 hours while distilling water and methanol away and while replenishing the same amount of distilled water through a dropping funnel. The reaction product was allowed to stand overnight, and then filtered off. The resulting crystal was washed with water and dried by a vacuum oven (60° C.), thereby to obtain 1002.3 g of 3-[hydroxy(phenyl)phosphinyl]propionic acid in the form of a white crystal (yield: 93.6%).

Analytical Values

Melting point 155° to 157° C. (%) 14.3 (Calculated value 14.5). Acid value (KOHmg/g) 523.2 (Calculated value 524.3). IR 3044 cm$^{-1}$ (—COOH), 1730 cm$^{-1}$ (—C=O), , 1600 cm$^{-1}$ ) —($C_6H_5$) NMR (1H–60 MHz ) δ: 1.6–2.7(m, 4H,—$CH_2CH_2$—), 7.4–8.1(m, 5H, —$C_6H_5$)

EXAMPLE 8

A 3-l four neck flask having a Dimroth condenser and a thermometer was charged with 895.0 g (5.0 moles) of dichloro(phenyl)phosphine, and heated under stirring to raise the liquid temperature to 55° C. Then, 367.5 g (5.1 moles) of acrylic acid was added dropwise to the mixture. To prevent heat from being generated, the reaction product was cooled with water to maintain the liquid temperature at 65° to 70° C. After the dropwise addition, the reaction was further continued at 70° to 75° C. for 2 hours.

With the liquid temperature lowered to 25° C., 510.0 g (5.0 moles) of acetic anhydride was added to the reaction product. After the reaction was carried out at 55° C. for 5 hours, the reaction product was distilled at the same temperature under reduced pressure to distill away acetyl chloride as a by-product and the residual acetic anhydride, thereby to obtain 948.7 g of 3-[hydroxy(phenyl)phosphinyl]propionic acid in the form of a cyclic anhydride (yield: 96.8%).

Analytical Values

Melting point 55.5° to 56.7° C. P (%) 15.6 (Calculated value 15.8).

EXAMPLE 9

First, 948.7 g of the cyclic anhydride obtained in Example 8 was added dropwise to 900 g of water (temperature at 55° C.), and was then heated at 100° C. for 3 hours. After cooled, the reaction product was filtered off. The resulting crystal was washed with water and dried by a vacuum oven (60° C.) , thereby to obtain 995.8 g of 3-[hydroxy(phenyl)phosphinyl]propionic acid in the form of a white crystal (yield: 93.0%).

Analytical Values

Melting point 155° to 157° C. P (%) 14.2 (Calculated value 14.5). Acid value (KOHmg/g) 523.1 (Calculated value 524.3). IR 3044 cm$^{-1}$ (—COOH), 1730 cm$^{-1}$ (C=O), 1600 cm$^{-1}$ (—C$_6$H$_5$). NMR (1H-60 MHz) δ: 1.6–2.7(m, 4H, —CH$_2$CH$_2$—), 7.4–8.1(m, 5H, —C$_6$H$_5$).

EXAMPLE 10

A 200-ml four neck flask having a Dimroth condenser and a thermometer was charged with 39.3 g (0.30 mole) of dichloro(ethyl)phosphine and 0.35 g (1.8× 10$^{-3}$ moles) of t-butyl peroxybenzoate, while carbonic acid gas was blown into the flask. Under stirring, the resulting mixture was heated to maintain the liquid temperature at 55° C. Then, 22.7 g (0.315 mole) of acrylic acid was added dropwise to the mixture. The reaction was carried out at 60° C. for 3 hours.

After the reaction, the liquid temperature was lowered to 50° C, and 60 g of water was gradually added to the reaction product. To prevent heat from being generated, the reaction product was cooled with ice water to maintain the liquid temperature at 60° to 70° C. After the dropwise addition, the reaction product was continuously stirred at the same temperature for 1 hour. After the liquid temperature was cooled to 10° C., the reaction product was filtered off and dried by a vacuum oven (60° C.), thereby to obtain 42.4 g of 3-[hydroxy(-phenyl)phosphinyl]propionic acid in the form of a white crystal (yield: 93.0%).

Analytical Values

Melting point 99.1° C. P (%) 18.4 (Calculated value 18.6). Acid value (KOHmg/g) 674.7 (Calculated value 675.4). IR 3044 cm$^{-1}$ (—COOH), 1730 cm$^{-1}$ (C=O). NMR (1H-60 MHz) δ: 1.6–2.7(m, 4H, —CH$_2$CH$_2$—).

What is claimed is:

1. A method of producing the resulting reaction product by the step comprising:

reacting a phosphine derivative of the following general formula I):

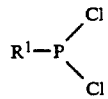
(I)

(wherein R$_1$ is an alkyl group having 1 to 18 carbon atoms or an aryl group having 6 to 18 carbon atoms, and said aryl group may have an alkyl group having 1 to 18 carbon atoms or an alkenyl group having 2 to 18 carbon atoms)

with acrylic acid or methacrylic acid in the presence of a catalyst selected from the group consisting of an organic peroxide and an azo-compound, said resulting reaction product having a chemical structure which:

(1), when hydrolyzed, changes to a phosphinyl-carboxylic acid derivative of the following general formula (III):

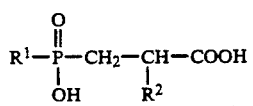
(III)

wherein R$^1$ is as defined above, and R$^2$ is a hydrogen atom or a methyl group, (2) when reacted with a hydroxyl group-containing compound of the following general formula (IV):

R$^3$—OH (IV)

(wherein R$^3$ is an alkyl group having 1 to 10 carbon atoms or an aryl group having 6 to 18 carbon atoms, and said aryl group may contain an alkyl group having 1 to 18 carbon atoms or an alkenyl group having 2 to 18 carbon atoms), changes to a phosphinyl-carboxylic acid derivative in the form of ester of the following general formula (V):

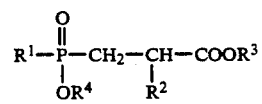
(V)

(wherein R$^1$ and R$^2$ are as defined above, R$^3$ is as defined above, R$^4$ is a hydrogen atom, an alkyl group having 1 to 10 carbon atoms or an aryl group having 6 to 18 carbon atoms, and said aryl group may contain an alkyl group having 1 to 18 carbon atoms or an alkenyl group having 2 to 18 carbon atoms), and (3) when reacted with acetic anhydride, changes to a phosphinyl-carboxylic acid derivative in the form of a cyclic acid anhydride of the following general formula (IV):

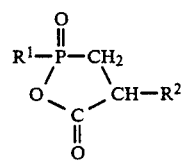
(VI)

(wherein R$^1$ and R$^2$ are as defined above).

2. A method of producing the resulting reaction product according to claim 1, wherein the compound of said formula (I) is admixed with said catalyst, and said methacrylic acid or said acrylic acid is then added dropwise to the mixture.

3. A method of producing the resulting reaction product according to claim 1, wherein said methacrylic acid or said acrylic acid is used in an amount of the same molar amount or more for the compound of said formula (I).

4. The reaction product formed by a process comprising the step of:

reacting a phosphine derivative of the following general formula (I):

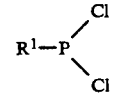
(I)

(wherein R$^1$ is an alkyl group having 1 to 18 carbon atoms or an aryl group having 6 to 18 carbon atoms, and said aryl group may have an alkyl group having 1 to 18 carbon atoms or an alkenyl group having 2 to 18 carbon atoms)

with acrylic acid or methacrylic acid in the presence of a catalyst selected from the group consisting of an organic peroxide and an azo-compound.

* * * * *